United States Patent
Lihl et al.

(10) Patent No.: US 10,217,603 B2
(45) Date of Patent: Feb. 26, 2019

(54) LOADING STATION FOR TRANSFERRING FROZEN SAMPLES AT LOW TEMPERATURES

(71) Applicant: Leica Mikrosysteme GmbH, Vienna (AT)

(72) Inventors: Reinhard Lihl, Vienna (AT); Leander Gaechter, Oberriet SG (CH)

(73) Assignee: Leica Mikrosysteme GmbH, Vienna (AT)

( * ) Notice: Subject to any disclaimer, the term of this patent is extended or adjusted under 35 U.S.C. 154(b) by 55 days.

(21) Appl. No.: 15/329,716

(22) PCT Filed: Jul. 15, 2015

(86) PCT No.: PCT/EP2015/066106
§ 371 (c)(1),
(2) Date: Jan. 27, 2017

(87) PCT Pub. No.: WO2016/016001
PCT Pub. Date: Feb. 4, 2016

(65) Prior Publication Data
US 2017/0213694 A1   Jul. 27, 2017

(30) Foreign Application Priority Data
Jul. 29, 2014 (DE) .......... 10 2014 110 722

(51) Int. Cl.
*H01J 37/20* (2006.01)
*H01J 37/26* (2006.01)
*H01J 37/18* (2006.01)
*G02B 21/00* (2006.01)
(Continued)

(52) U.S. Cl.
CPC ............... *H01J 37/20* (2013.01); *G01N 1/42* (2013.01); *G02B 21/00* (2013.01); *H01J 37/18* (2013.01);
(Continued)

(58) Field of Classification Search
CPC .. H01J 37/20; H01J 37/26; H01J 37/18; H01J 2237/16; H01J 2237/20221; H01J 2237/262; G01N 1/42; G02B 21/00
(Continued)

(56) References Cited

U.S. PATENT DOCUMENTS 5,352,898 A * 10/1994 Mehta .............. G01N 1/286
250/304
2003/0003577 A1   1/2003 Horstmann
(Continued)

FOREIGN PATENT DOCUMENTS

WO   2009/145377 A1   12/2009

OTHER PUBLICATIONS

Leica Microsystems GmbH, product brochure: Leica EM VCT100 Vacuum Cryo Transfer, May 2009.
(Continued)

*Primary Examiner* — Nicole Ippolito
(74) *Attorney, Agent, or Firm* — Hodgson Russ LLP

(57) ABSTRACT

A loading station (100, 200) for translocating a frozen sample for electron microscopy, encompassing a chamber (104, 204), open toward the top, that is fillable at least partly with a coolant, the chamber (104, 204) comprising in its side wall at least two ports (101a, 102a, 103a) each for different sample transfer devices (101, 102, 103), the ports (101a, 102a, 103a) permitting introduction of a frozen sample into the chamber (104, 204) via a selected sample transfer device and withdrawal of a frozen sample from the chamber via a respective different sample transfer device; and wherein a receptacle (108, 208) for at least two differently configured sample holders (109, 110) is arranged in the chamber (104, 204), the at least two sample holders (109, 110) being detachably fastenable to at least one of the sample transfer devices (101) for introduction of the frozen sample into the chamber (104, 204) and for withdrawal of the frozen sample from the chamber (104, 204).

11 Claims, 6 Drawing Sheets

(51) Int. Cl.
*G01N 1/42* (2006.01)
*G01N 1/06* (2006.01)
*G01N 1/32* (2006.01)

(52) U.S. Cl.
CPC ................ *H01J 37/26* (2013.01); *G01N 1/06* (2013.01); *G01N 1/32* (2013.01); *H01J 2237/16* (2013.01); *H01J 2237/20221* (2013.01); *H01J 2237/262* (2013.01)

(58) Field of Classification Search
USPC ................ 250/440.11, 441.11, 442.11, 443.1
See application file for complete search history.

(56) References Cited

U.S. PATENT DOCUMENTS

| | | | |
|---|---|---|---|
| 2008/0239283 A1 | 10/2008 | Tamura et al. | |
| 2009/0183613 A1 | 7/2009 | Lihl et al. | |
| 2009/0230319 A1* | 9/2009 | Fujiyoshi | ................ H01J 37/20 250/442.11 |
| 2011/0027876 A1* | 2/2011 | Lihl | ........................ G01N 1/42 435/307.1 |

OTHER PUBLICATIONS

Gatan Inc., product sheet: Single Tilt Liquid Nitrogen Cryo Transfer Holder Model 626, Dec. 2103.

Hsieh, Chyongere, et al., "Practical workflow for cryo focused-ion-beam milling of tissues and cells for cyo-TEM tomography," Jornal of Structural Biology, vol. 185, pp. 32-41, Nov. 6, 2013.

* cited by examiner

LOADING STATION FOR TRANSFERRING FROZEN SAMPLES AT LOW TEMPERATURES

CROSS-REFERENCE TO RELATED APPLICATIONS

The present application is the U.S. national phase of International Application No. PCT/EP2015/066106 filed Jul. 15, 2015, which claims priority of German Application No. 10 2014 110 722.5 filed Jul. 29, 2014, the entirety of which is incorporated herein by reference.

FIELD OF THE INVENTION

The invention relates to a loading station for translocating a frozen sample for electron microscopy, encompassing a chamber, open toward the top, that is fillable at least partly with a coolant.

BACKGROUND OF THE INVENTION

Cryofixation is a sample preparation method often used in electron microscopy. In this, a water-containing sample is frozen very rapidly to a temperature below −150° C. (cryofixed), i.e. it is cooled very quickly while avoiding the formation of ice crystals. Cryofixation has proven to be particularly suitable for investigations of structural biology. The specimens to be investigated, for example cells, enzymes, viruses, or lipid layers, are thereby embedded in a thin, vitrified layer of ice. The great advantage of cryofixation is that the biological structures can be maintained in their natural state. For example, a biological process can be halted at any arbitrary point in time by cryofixation and investigated in that vitrified state, for example using a cryo-electron microscope and/or in a light microscope with corresponding sample cooling. Correlative methods between a light microscope and electron microscope, also referred to as "CLEM" (correlative light-electron microscopy), make it possible, for example, firstly to observe a biological sample in a light microscope until the desired state is reached. The sample is then transferred into a cryopreparation apparatus and cryofixed for electron microscopy observation. In another variant of CLEM, the light-microscopy investigation is performed on the already cryofixed sample. Cryofixed samples can furthermore also be subjected, in a manner known per se, to further preparation steps, for example processing using freeze-fracture technology (freeze-etching) and/or coating techniques.

In order not to impair the quality of the frozen samples, it is very important that they be transferred in cooled and contamination-free fashion between the processing devices being used (for example cryofixation device, freeze fracture apparatus, coating apparatus), and the analysis devices (e.g. cryo-electron microscope, cooled light microscope).

The brochure for the "Leica EM VCT100" vacuum cryo-transfer system (manufacturer: Leica Microsystems), which is accessible via the link http://leica-microsystems.com/fileadmin/downloads/Leica%20EM%20VCT100/Brochures/Leica_EMVCT100_Brochure_EN.pdf, discloses a liquid nitrogen-cooled loading station to which a transfer container (Leica EM VCT100 Shuttle) can be coupled. A sample holder is detachably fastenable to a slide rod of the transfer container. The sample holder can be transferred out of the cooled transfer container into a cooled chamber of the loading station by displacement of the slide rod. A receptacle for retaining the sample holder is arranged inside the chamber of the loading station. The very small frozen electron microscopy samples, which are usually located in a manner known per se on an electron microscopy sample carrier (e.g. a grid or a pin for scanning electron microscopy), are manually introduced into the liquid nitrogen-cooled chamber of the loading station. The sample carrier having the sample is removed, for example with a forceps, and fastened in the sample holder. This process occurs in a cooled state, so that the frozen sample does not thaw or melt and thus become unusable. The transfer container having the sample holder and the sample carrier with a sample is then uncoupled from the loading station and attached to a corresponding apparatus (e.g. freeze fracture apparatus, cryo-electron microscope) for further processing or analysis.

The number and capabilities of sample processing operations, analyses, and corresponding devices in electron microscopy is constantly increasing. Translocation of the sample into a differently configured sample holder, or into a differently configured sample transfer device, is normally also necessary for the various applications. With the known loading station described above, translocation of a sample from one sample holder into a differently configured sample holder for a different application is not possible. It is also possible to attach only a single transfer container. Users therefore usually make do by transporting the sample to various installation sites in small containers and in liquid nitrogen. This not only involves a considerable expenditure of time, but encompasses critical working steps in which the samples can become damaged or contaminated. The working step in which the error occurred is then often not perceptible. The known loading station furthermore has no temperature monitoring, and coolant replenishment occurs manually.

SUMMARY OF THE INVENTION

An object of the invention is therefore to make possible maximally contamination-free translocation of a frozen sample from one sample holder into a differently configured sample holder, or into a differently configured sample transfer device, which is provided for a different application.

This object is achieved with a loading station of the kind recited previously, which according to the present invention is characterized in that the chamber comprises in its side wall at least two ports each for different sample transfer devices, the ports permitting introduction of a frozen sample into the chamber via a selected sample transfer device and withdrawal of a frozen sample from the chamber via a respective different sample transfer device; and that a receptacle for at least two differently configured sample holders is arranged in the chamber, the at least two sample holders being detachably fastenable to at least one of the sample transfer devices for introduction of the frozen sample into the chamber and for withdrawal of the frozen sample from the chamber.

Thanks to the invention, very largely contamination-free and time-saving translocation of frozen samples for electron microscopy between the (usually differently configured) sample holders of the individual processing devices or analysis devices, at temperatures below −150° C., is possible.

In most cases the frozen sample is mounted on an electron microscopy sample carrier, the conformation of which depends on the respective application. The term "sample carrier" therefore refers to all carriers suitable for electron microscopy and for electron microscopy sample preparation. Sample carriers for electron microscopy are sufficiently familiar to one skilled in the art. They are, for example, pin-like carriers for scanning electron microscopy, or small mesh-shaped carriers that are generally referred to as "grids." The grids can comprise variously shaped holes (honeycombs, slits, etc.) or a lattice of a defined mesh size, and/or can be coated with a film (e.g. coated grids of the Quantifoil company) and/or can be carbon vapor-coated. Other carriers that are likewise used in cryopreparation of electron microscopy samples are, for example, sapphire disks as described in EP 1 267 164 B1.

The sample carrier having the sample can in turn be detachably fastened in a sample holder of the sample transfer device. The sample holder either can be fixedly connected to the sample transfer device (e.g. a sample holder for transmission electron microscopy, such as a cryo-TEM holder of the Gatan company (model 626 single tilt liquid nitrogen cryo-transfer holder)), or it can be detachably couplable to the sample transfer device and can therefore be replaceable. One known sample transfer device, on which variously configured sample holders that are each used for different applications, is the Leica EM VCT100 Shuttle (manufacturer: Leica Microsystems) already recited above. The Leica EM VCT100 Shuttle is also suitable for attachment to the loading station in accordance with the invention. The sample holder that can be coupled to the Leica EM VCT100 Shuttle is selected depending on the sample carrier being used (e.g. a grid). Alternatively thereto, certain applications provide that the sample is mounted directly on a surface of the sample holder, i.e. with no sample carrier such as a grid.

The frozen samples are very small electron microscopy samples that can be translocated by means of the loading station according to the present invention into the different sample holders of the various processing devices or analytical devices. In the context of the correlative methods between a light microscope and electron microscope already mentioned above (CLEM, correlative light-electron microscopy), the frozen electron microscopy samples are investigated using both a light microscope and an electron microscope. The loading station according to the present invention also enables simple translocation of a frozen electron microscopy sample into sample holders that are embodied for light and electron microscopy.

Usefully, the receptacle for the at least two differently configured sample holders is arranged in a floor region of the chamber.

In an advantageous refinement, the receptacle encompasses a rotatable and tiltable spherical segment on which at least two differently configured sample holders are receivable. The sample holders are thus retained detachably in the receptacle. In a sub-variant, the receptacle is provided for exactly two differently configured sample holders, the spherical segment enabling a rotation around a vertical axis and a tilt. Alternatively thereto, the receptacle can also receive more than two sample holders, for example a receptacle on which four sample holders can be retained crosswise.

In another refinement, the receptacle encompasses a displaceable carriage on which at least two differently configured sample holders are receivable.

In an advantageous refinement, the loading station is characterized by a reservoir container for the coolant, which is connected to the chamber via a controllable inlet valve for the coolant. The controllable inlet valve is controlled, for example, via a stepping motor. Advantageously, a fill level sensor, with which coolant delivery from the reservoir container into the chamber is regulatable via the controllable inlet valve, is arranged in the chamber. Regulation of the coolant delivery into the chamber guarantees automatic replenishment of the coolant into the chamber, and thus continuous cooling of the samples.

The loading station can furthermore comprise a temperature monitoring system, for example by way of a temperature sensor positioned in the chamber.

Regulation of coolant delivery by means of the fill level sensor and the controllable inlet valve, and temperature monitoring by way of the temperature sensor, are accomplished using a control system that is constructed in a manner known per se and typically comprises a microcontroller as well as electronic components.

Fill level deviations and temperature deviations in the chamber that go beyond a respective predefinable temperature range and fill level range can be compensated for by the control system. It is furthermore also possible for deviations to be brought to an operator's attention as an alarm signal.

The loading station can furthermore encompass an operating console for the input of instructions for the control system. Such instructions encompass, for example, the programming of coolant delivery and of temperature.

The coolant (also referred to as a "cryogen") is a liquefied gas such as liquid nitrogen (LN2) or liquid air, preferably liquid nitrogen.

The chamber of the loading station is configured to be open toward the top. Continuous evaporation of the coolant results in formation of a flow of cold gas that emerges from the chamber and thus prevents air from entering. In the context of a particularly advantageous variant, the loading station comprises a breath shield that is positioned above the chamber that is open toward the top. The breath shield prevents water vapor from freezing in or on the chamber. The emerging flow of cold gas and the breath shield prevent contamination of the samples.

In an advantageous variant, an air lock, which by means of a vacuum pump respectively permits evacuation of a sample transfer device as well as transfer of the frozen sample into an evacuatable sample transfer device and transfer of the frozen sample out of an evacuatable sample transfer device, is attachable to the chamber. Transfer under vacuum prevents contamination, and ensures better cooling of the sample (heat transfer only by radiation; almost no gas convection). One sample transfer device that is provided for cryo-transfer of frozen samples under vacuum or in an inert gas atmosphere is the aforementioned Leica EM VCT100 Shuttle (manufacturer: Leica Microsystems). Sample transfer devices for cryo-transfer under vacuum or in inert gas possess a container that, for transfer, is evacuated or can be filled with inert gas. The frozen samples are transferred into and out of the container via an air lock. Air locks of this kind are known per se and, for example, are constructed so that they are delimited by two slide valves, a vacuum being producible in the cavity between the slide valves by corresponding positioning of the slide valves. One slide valve can be fastened on the sample transfer device; the other slide valve is fastened on the loading station port. The air lock is formed by docking the sample transfer device onto the loading station port, for example via a hooking apparatus, and is sealed off from the outside, for example, by means of O-rings. The sample transfer device advantageously possesses a slide rod on which the sample holder having a sample is secured. The sample holder can then be transferred by means of the slide rod through the air lock from the loading station into the sample transfer device, and vice versa.

In a variant, at least one of the ports is configured as a port for a sample transfer device that is provided for cryo-transfer of frozen samples under vacuum or in an inert gas atmosphere. One example of such a sample transfer device is the Leica EM VCT100 Shuttle (manufacturer: Leica Microsystems) recited above.

In a further variant, at least one of the ports is configured as a port for a sample transfer device for transmission electron microscopy (TEM), for example as a cryo-TEM container sufficiently known to one skilled in the relevant art. Cryo-TEM holders are manufactured, for example, by the Gatan company (model 626 single tilt liquid nitrogen cryo-transfer holder). The port typically encompasses a continuous orifice and a fitting for the cryo-TEM holder. The orifice can be closed off, for example, with a stubble.

In a further variant, at least one of the ports is configured as a port for a sample transfer device for light microscopy. This variant enables translocation of frozen electron microscopy samples from sample holders for electron microscopy into a sample holder for a light microscope, and is utilized especially in the correlative methods already mentioned previously which use both light microscopy and electron microscopy (CLEM). After translocation and transfer out of the chamber of the loading station, the frozen samples can be investigated by light microscopy with the aid of special cooled stages.

BRIEF DESCRIPTION OF THE DRAWING VIEWS

The invention will be explained in more detail below with reference to a non-limiting example that is depicted in the attached drawings, in which.

DETAILED DESCRIPTION OF THE INVENTION

Figure 1:
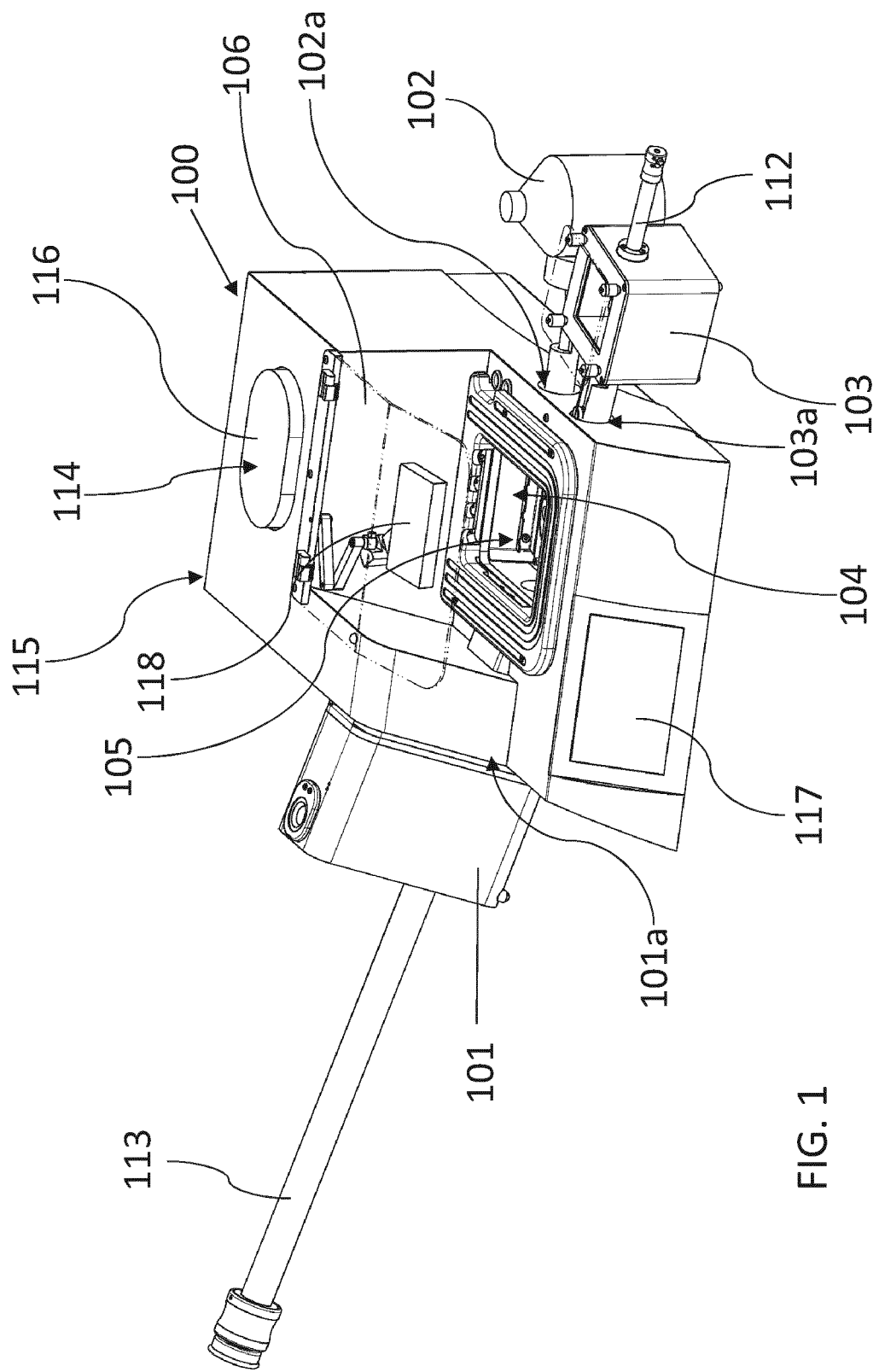
FIG. 1 is a perspective view of a loading station according to the present invention.
Figure 2:
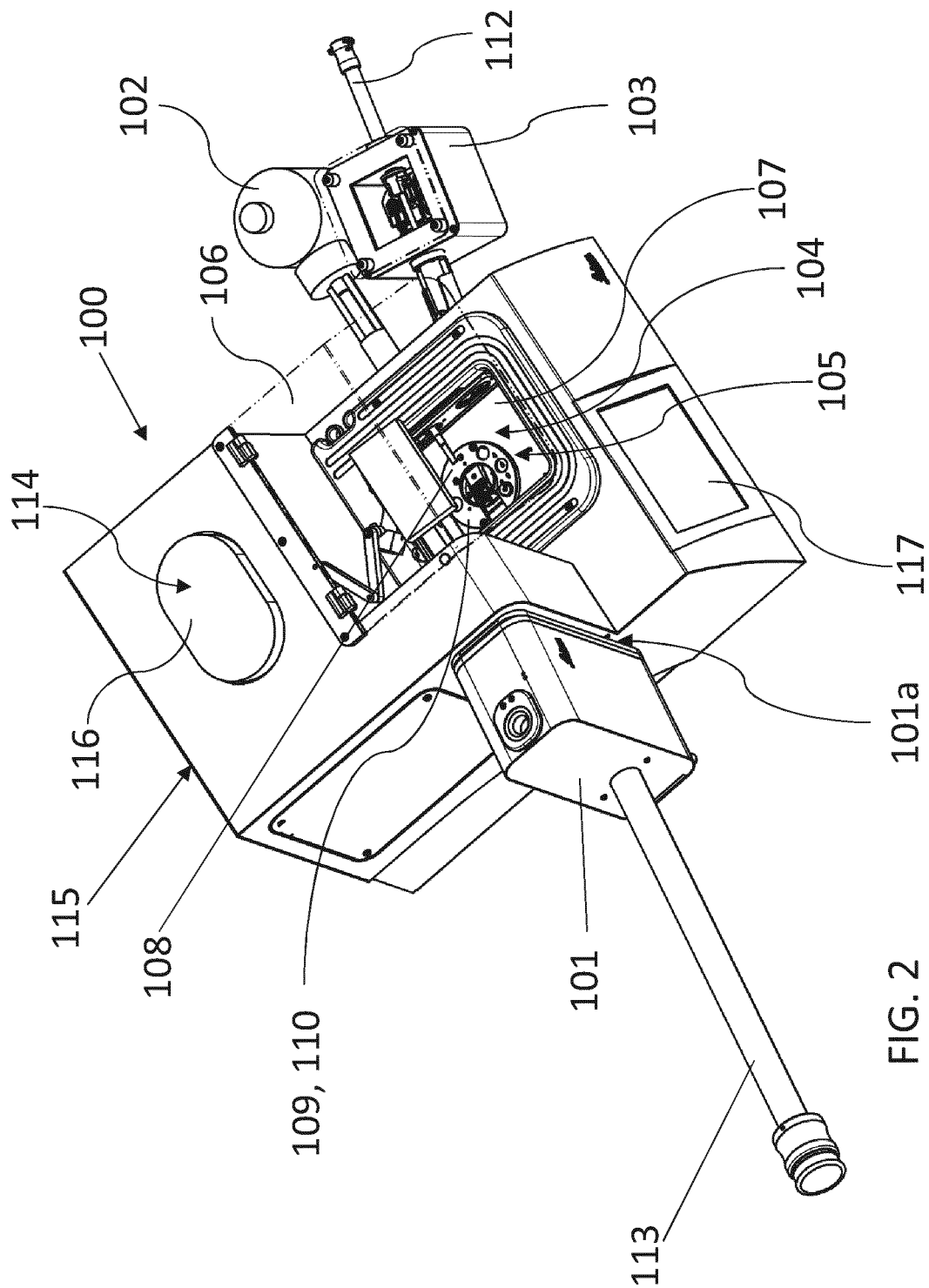
FIG. 2 is a further perspective view of the loading station of FIG. 1 from a different viewing angle.

FIG. 1 and FIG. 2 are perspective views of a loading station 100 in accordance with the invention. Loading station 100 encompasses a chamber 104, cooled with coolant (in the example, liquid nitrogen (LN2)), which is open toward the top. In the example shown, chamber 104 is embedded into a housing 115. Chamber 104 is filled at least partly with LN2. Continuous evaporation of the coolant results in formation of a flow of cold gas that emerges from chamber 104 and thereby prevents the entry of air. A breath shield 106 is positioned above open region 105 of chamber 104. The breath shield prevents water vapor from freezing in or on the chamber. The emerging flow of cold gas, and the breath shield, thus prevent contamination of the samples.

The loading station furthermore possesses a magnifying lens (loupe) 118 that is positioned above chamber 104 and below breath shield 106.

The samples are very small frozen samples for electron microscopy, which are transferred into and out of chamber 104 in the frozen state at less than −150° C. and are translocated in chamber 104.

Figure 3:
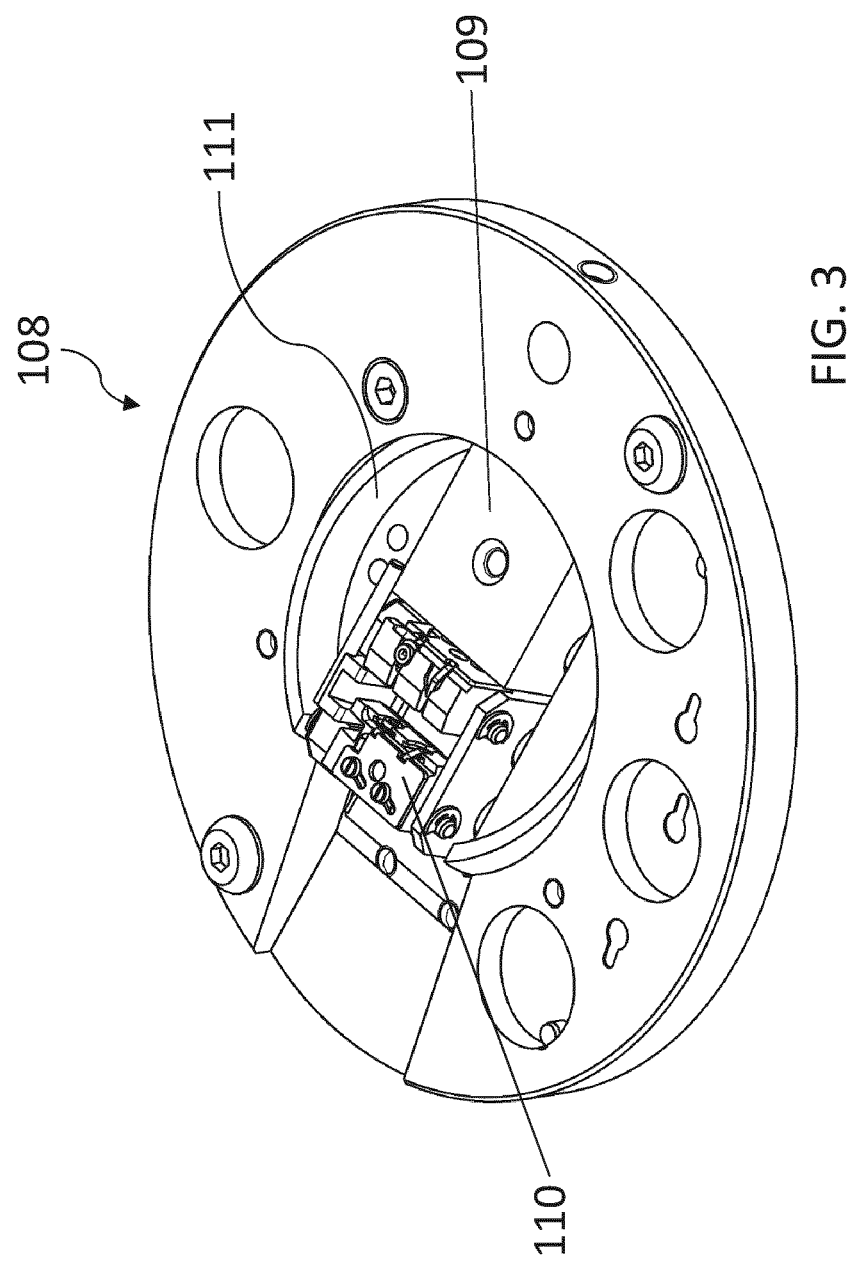
FIG. 3 is an enlarged perspective view of the receptacle for sample holders of the loading station depicted in FIG. 1 and FIG. 2.

A receptacle 108 for two sample holders 109, 110, which are configured to hold frozen samples, is arranged on chamber floor 107. Receptacle 108, which is shown enlarged in FIG. 3, is arranged on a spherical segment 111. Spherical segment 111 is mounted tiltably and rotatably around a vertical axis, and can snap-lock into various positions by way of springs (not shown in further detail).

Returning to FIGS. 1 and 2: chamber 104 comprises in its side walls a total of three ports 101a, 102a, and 103a respectively for three different transfer devices 101, 102, and 103. Transfer devices 101, 102, and 103 are attached from outside to ports 101a, 102a, and 103a. Ports 101a, 102a, 103a encompass openings through which frozen electron microscopy samples can be introduced from transfer devices 101, 102, 103 into the chamber and withdrawn. Unused ports are each closed off by a slider (not depicted in further detail).

In the example depicted, transfer device 101 is the Leica EM VCT100 Shuttle (manufacturer: Leica Microsystems) mentioned above, i.e. a transfer container that is provided for cryo-transfer of frozen samples under vacuum or in an inert gas atmosphere. Transfer device 101 possesses a slide rod 113 with which a sample holder can be introduced from the cooled transfer device 101, through the opening of port 101a, into chamber 104. Transfer of the sample into and out of transfer device 101 occurs via an air lock 119 described in detail below in FIGS. 5 and 6.

In the example depicted, transfer device 103 is a transfer device for light microscopy, and likewise possesses a slide rod 112 with which a sample holder can be introduced through the opening of port 103a into chamber 104.

Transfer device 102 is a cryo-TEM sample holder (e.g. model 626 single tilt liquid nitrogen cryo-transfer holder of the Gatan company), in which that end of the TEM specimen holder in which the sample is received can be inserted through the opening of port 102a into chamber 104.

Loading station 100 shown in the example possesses a total of three different ports for three different transfer devices. There can also be, however, only two different ports or also more than three different ports, for example four or five different ports. The number and respective configuration of the ports depend on the transfer containers to be attached; the combination of the type of port and the transfer container is correspondingly selected depending on the application spectrum.

In the example depicted, only transfer device 101 communicates with receptacle 108 for sample holder 109, 110. Tilting of receptacle 108 with the aid of the rotatable and tiltable spherical segment 111 is necessary because transfer device 101 is placed obliquely onto loading station 100 (see FIG. 2); and for translocation of the sample, sample holder 109 or 110 is uncoupled from slide rod 113 via a bayonet, immobilized in receptacle 108, and only then brought into a horizontal processing position.

The translocation of a sample from sample holder 109 to the different sample holder 110 will be described below. In FIGS. 2 and 3, sample holders 109, 110 are retained in receptacle 108, sample holder 109 being directed toward transfer device 101 and having previously been uncoupled therefrom. A sample located in sample holder 109 can then be translocated manually, e.g. with a forceps, into sample holder 110. A selection of sample holders for various applications in scanning electron microscopy (SEM) is presented in the brochure for the "Leica EM VCT100" vacuum cryo-transfer system (manufacturer: Leica Microsystems), which is accessible via the link http://leica-microsystems.com/fileadmin/downloads/Leica%20EM%20VCT100/Brochures/Leica_EMVCT100_Brochure_EN.pdf. The analytical and processing methods used in electron microscopy are very varied, and the configuration of the sample holders is correspondingly varied.

After translocation, spherical segment 111 is rotated 180° so that sample holder 110 is now directed toward transfer device 101. Spherical segment 111 is then tilted, and sample holder 110 having the sample can then be coupled onto that end 113a of slide rod 113 which extends into chamber 104, and removed from chamber 104 by pulling slide rod 113 back. Alternatively thereto, the sample can also be translocated from sample holder 109 into the respective sample mounts of transfer devices 102 and 103 for other analytical or processing steps.

Loading station 100 furthermore comprises a reservoir container 114 for coolant, which container is likewise embedded into housing 115. Reservoir container 114 can be closed off with a cover 116. Reservoir container 114 is connected to chamber 104 via a controllable inlet valve (not depicted in further detail) for coolant. The controllable inlet valve is embodied in a manner known per se and is controlled, for example, via a stepping motor. Also arranged in chamber 104 is a fill level sensor, embodied in a manner known per se and likewise not depicted, with which coolant delivery from reservoir container 114 into chamber 104 is regulatable by way of the controllable inlet valve. Regulation of coolant delivery into chamber 104 ensures automatic replenishment of coolant into chamber 104, and thus continuous cooling of the samples. Loading station 100 furthermore comprises a temperature monitoring system of a kind known per se, for example a temperature sensor positioned in the chamber.

Regulation of coolant delivery by means of the fill level sensor and the controllable inlet valve, and temperature monitoring by way of the temperature sensor, are accomplished using a control system (not depicted in further detail) that is configured in a manner known per se and typically comprises a microcontroller as well as electronic components. Fill level deviations and temperature deviations in chamber 104 that go beyond a respective predefinable temperature range and fill level range can be compensated for by the control system. It is furthermore also possible for deviations to be brought to an operator's attention as an alarm signal, for example as an optical or acoustic alarm signal.

Loading station 100 furthermore encompasses an operating console for the input of instructions for the control system. Such instructions encompass, for example, programming of coolant delivery and of temperature.

Figure 4:
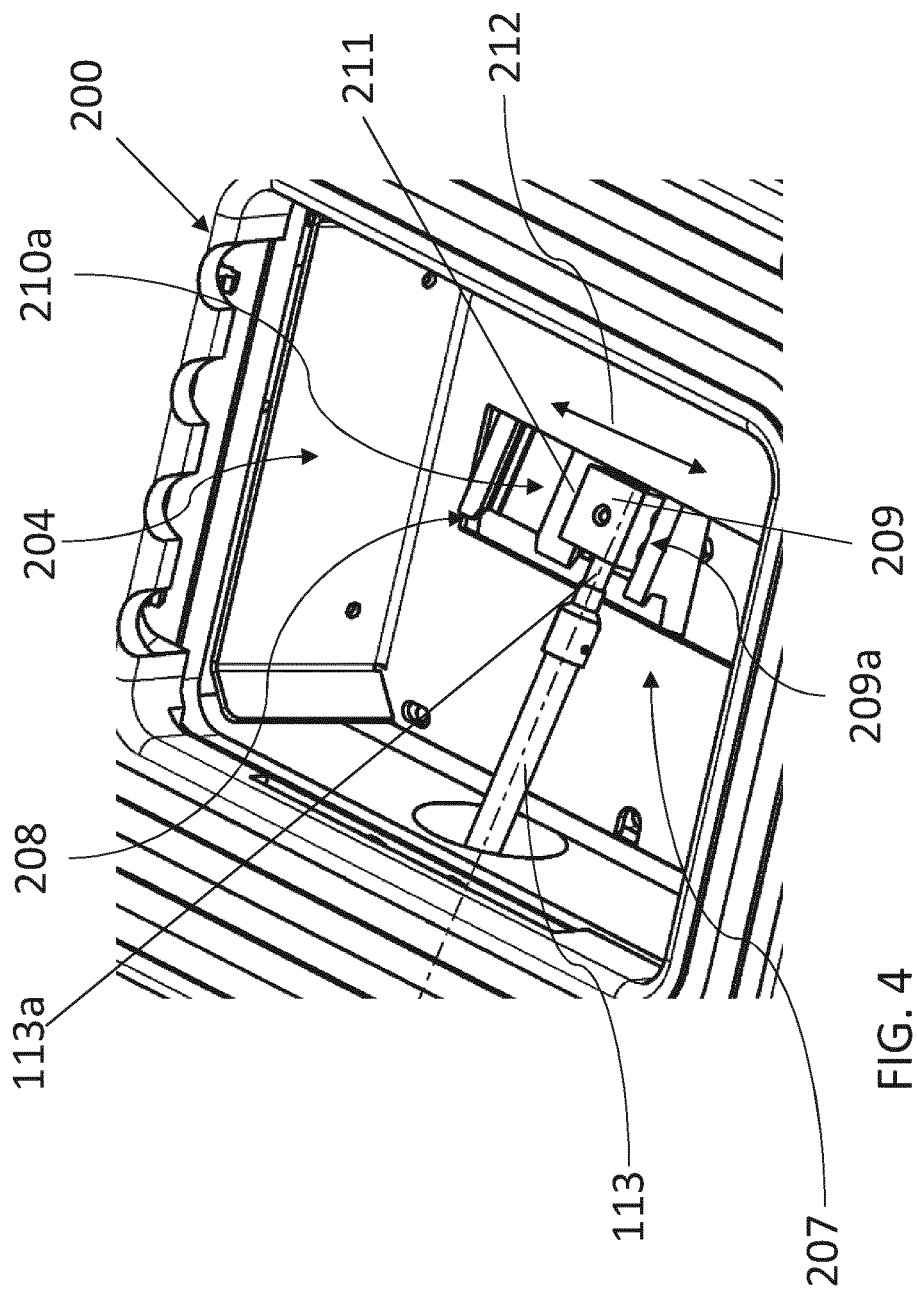
FIG. 4 is a perspective view of an alternative embodiment of the receptacle for sample holders.

FIG. 4 is a perspective view of an alternative embodiment of a receptacle 208 for sample holders. Receptacle 208 is arranged on chamber floor 207 of a chamber 204 of a loading station 200. Except for receptacle 208, the construction of loading station 200 otherwise corresponds to that of loading station 100. Receptacle 208 shown in FIG. 4 encompasses a slider 211 in the manner of a carriage, in which a total of two sample holders are retainable. In FIG. 4 only one sample holder 209 is detachably fastened in a first retention position 209a of receptacle 208; the second retention position 210a for sample holder 210 (not depicted) is unoccupied. Sample holders 209, 210 are embodied like sample holders 109, 110 described above. Slider 211 is mounted tiltably in order to couple sample holders 209, 210 to that end 113a of slide rod 113 of transfer device 101 which extends into chamber 204. By displacing slider 211 in a direction that is indicated by arrow 212, it is possible to position the respective sample holder 209, 210 with respect to slide rod 113.

Figure 5:
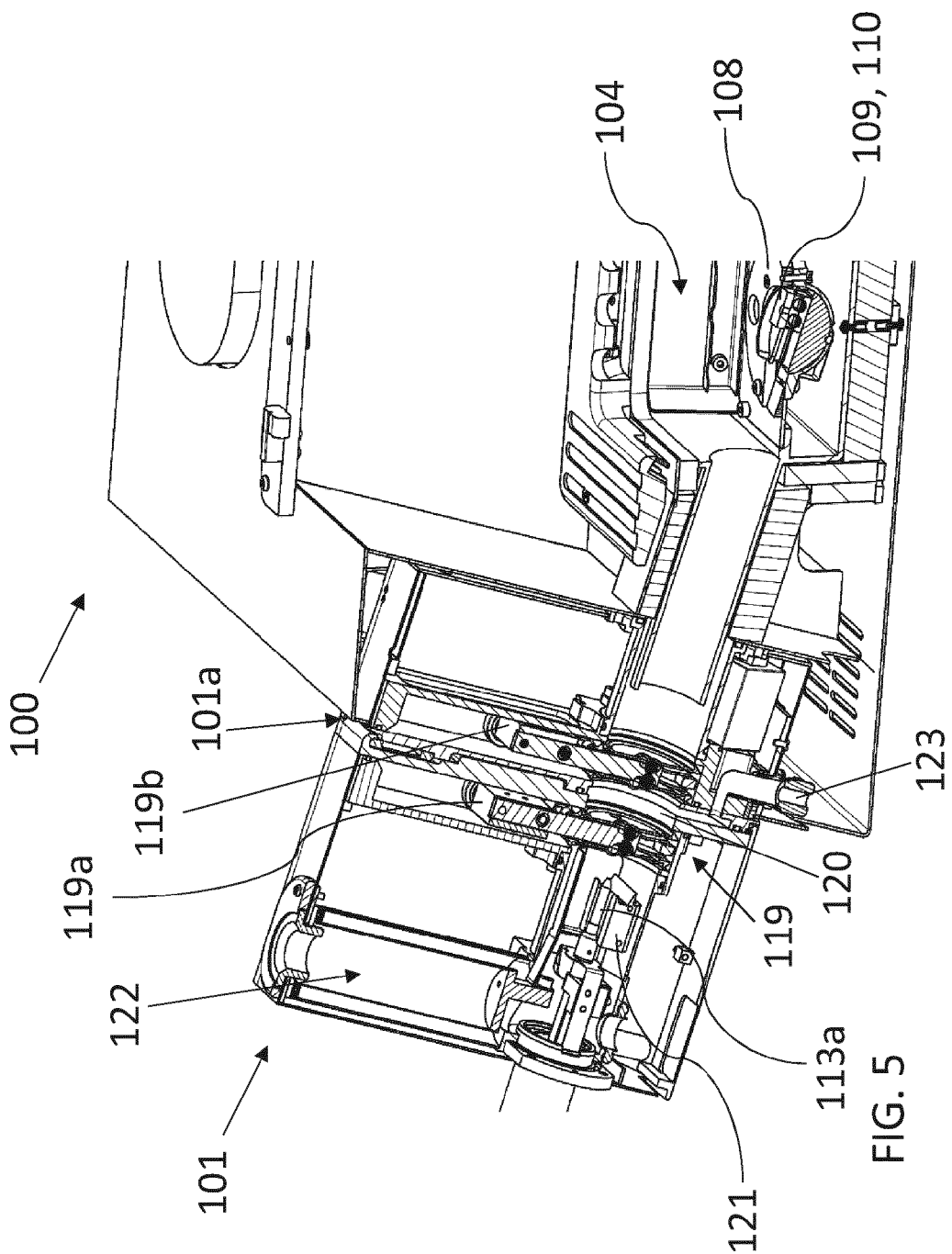
FIG. 5 is an enlarged view of a section through the loading station and the transfer device for cryo-vacuum transfer of FIG. 1.
Figure 6:
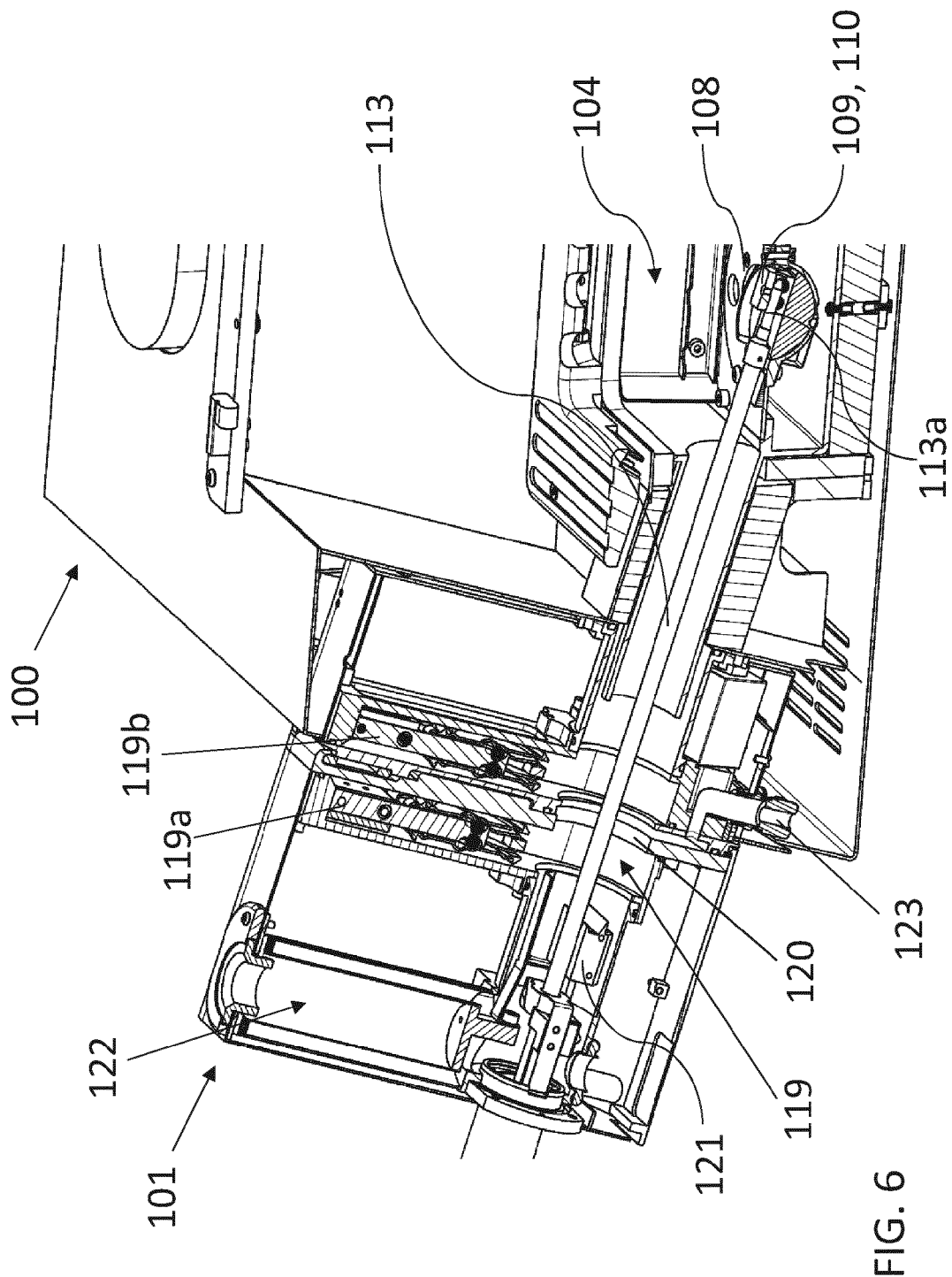
FIG. 6 is an enlarged view of a further section through the loading station and the transfer device for cryo-vacuum transfer of FIG. 1.

FIGS. 5 and 6 are enlarged views of sections through loading station 100 and transfer device 101 of FIG. 1. As described above, transfer device 101 is the Leica EM VCT100 Shuttle (manufacturer: Leica Microsystems), i.e. a transfer container that is provided for cryo-transfer of frozen samples under vacuum or in an inert gas atmosphere. With the aid of slide rod 113 of transfer device 101, a sample holder can be introduced from the cooled transfer device 101 through the opening of port 101a, via an airlock 119, into chamber 104 of loading station 100.

Air lock 119 encompasses two vacuum sliders 119a, 119b. A vacuum can be created in cavity 120 between vacuum sliders 119a, 119b, or in the interior of transfer device 101, by corresponding positioning of vacuum sliders 119a, 119b. Loading station 100 possesses a pump port 123 for a vacuum pump (not depicted in further detail) for respectively pumping out transfer device 101 and pumping out cavity 120. Vacuum slider 119a is fastened on sample transfer device 101; vacuum slider 119b is fastened on port 101a of loading station 100. Air lock 119 is formed by docking sample transfer device 101 onto port 101a of loading station 100.

FIG. 5 shows the two vacuum sliders 119a, 119b in a closed position. End 113a of slide rod 113 is pulled back into transfer device 101. In this depiction, a sample holder 109, 110 is not located at present in transfer device 101; sample holders 109, 110 are positioned in the rotatable and tiltable spherical segment 111 of receptacle 108 (see also FIG. 3 in this context). In order to introduce a sample present on a sample holder 109, 110 from loading station 100 with the aid of slide rod 113, vacuum sliders 119a, 119b are opened. This is evident from FIG. 6, in which both vacuum sliders 119a, 119b are shown in an open position and slide rod 113 of transfer device 101 is advanced through air lock 119 into chamber 104 of loading station 100. Sample holder 109 or 110 having the sample can now be fastened on end 113a of slide rod 113 and then pulled back into transfer device 101. Vacuum slider 119b is then closed, and transfer device 101 can be pumped out by means of the vacuum pump via pump port 123. Vacuum slider 119a is then also closed. Lastly, cavity 120 between sliders 119a, 119b can be aerated again, and transfer device 101 can be uncoupled from loading station 100 in order to transfer the sample into a processing device and/or analytical device.

For transferring a sample out of an evacuated transfer device 101 into a processing device and/or analytical device, transfer device 101 is usually not aerated, since the processing device and/or analytical device is usually also under vacuum. Located on the processing device and/or analytical device is a port for transfer device 101 having a closed vacuum slider that corresponds in terms of construction to vacuum slider 119b. Upon docking of transfer device 101 onto the processing device and/or analytical device, an air lock in accordance with air lock 119 described above is therefore once again formed. After the docking of transfer device 101, the cavity between the two vacuum sliders 119a, 119b is pumped out and both vacuum sliders are then opened. Transfer of the sample out of transfer device 101 into the processing device and/or analytical device is accomplished with the aid of slide rod 113 under vacuum.

As is also evident from FIGS. 5 and 6, transfer device 101 furthermore possesses, for cooling the sample, a coolant reservoir 122 (Dewar vessel 122) that can be filled with a coolant, typically liquid nitrogen. In order to cool the sample, Dewar vessel 122 is connected in a manner known per se, via thermally conductive copper components, to a cooled specimen stage 121 arranged in the interior of transfer device 101. Sample holder 109, 110 having the sample is positioned on the cooled specimen stage 121 during the transfer between loading station 100 and a processing device and/or analytical device.

The example shown is only one among many, and is not to be construed as limiting.

PARTS LIST

100 Loading station
101 Transfer device for cryo-transfer under vacuum or in inert gas atmosphere
102 Transfer device for transmission electron microscopy
103 Transfer device for light microscopy
101a Port for transfer device 101
102a Port for transfer device 102
103a Port for transfer device 103
104 Chamber
105 Open region of chamber 104
106 Breath shield
107 Chamber floor
108 Receptacle for sample holders encompassing a tiltable and rotatable spherical segment 111
109 Sample holder
110 Sample holder
111 Tiltable and rotatable spherical segment
112 Slide rod of transfer device 103
113 Slide rod of transfer device 101
113a End of slide rod for transfer device 101
114 Reservoir container for coolant
115 Housing
116 Cover of reservoir container for coolant
117 Operating console
118 Magnifying lens
119 Air lock
119a Vacuum slider
119b Vacuum slider
120 Cavity between vacuum sliders 119a and 119b
121 Specimen stage
122 Dewar vessel
123 Pump port for a vacuum pump
200 Loading station
207 Chamber floor
208 Receptacle for sample holders encompassing a slider 211
209 Sample holder
210 Sample holder
209a Retention position for sample holder 209
210a Retention position for sample holder 210
211 Slider
212 Displacement direction of slider 211

What is claimed is:

1. A loading station (100, 200) for translocating a frozen sample for electron microscopy, comprising a chamber (104, 204) having an open top, a floor (107, 207) opposite the open top, and at least one side wall extending between the floor and the open top, the chamber (104, 204) being fillable at least partly with a coolant,
wherein the chamber (104, 204) comprises in the at least one side wall thereof at least two ports (101a, 102a, 103a) respectively for different sample transfer devices (101, 102, 103), the ports (101a, 102a, 103a) permitting introduction of a frozen sample into the chamber (104, 204) via a selected sample transfer device and withdrawal of the frozen sample from the chamber via another sample transfer device; and wherein a receptacle (108, 208) for at least two differently configured sample holders (109, 110; 209, 210) is arranged in the chamber (104, 204), the at least two sample holders (109, 110; 209, 210) being detachably fastenable to at least one of the sample transfer devices (101) for introduction of the frozen sample into the chamber (104, 204) and for withdrawal of the frozen sample from the chamber (104, 204).

2. The loading station according to claim 1, wherein the receptacle (108, 208) is arranged in a floor region (107, 207) of the chamber (104, 204).

3. The loading station according to claim 1, wherein the receptacle (108) comprises a rotatable and tiltable spherical segment (111) on which the at least two differently configured sample holders (109, 110) are receivable.

4. The loading station according to claim 1, wherein the receptacle (208) comprises a displaceable carriage (211) on which the at least two differently configured sample holders (209, 210) are receivable.

5. The loading station according to claim 1, further comprising a reservoir container (114) for the coolant, the reservoir container (114) being connected to the chamber (104, 204) via a controllable inlet valve for the coolant.

6. The loading station according to claim 5, further comprising a fill level sensor arranged in the chamber (104, 204), wherein coolant delivery from the reservoir container (114) into the chamber (104, 204) is regulatable via the controllable inlet valve based on a coolant fill level detected by the fill level sensor.

7. The loading station according to claim 6, further comprising a breath shield (106) positioned above the chamber (104, 204).

8. The loading station according to claim 1, further comprising an air lock attachable to the chamber (104), wherein the air lock enables evacuation of a sample transfer device by means of a vacuum pump and transfer of the frozen sample into the evacuated sample transfer device and transfer of the frozen sample out of the evacuated sample transfer device.

9. The loading station according to claim 1, wherein at least one of the ports (101a) is configured as a port for a sample transfer device (101) for cryo-transfer of frozen samples under vacuum or in an inert gas atmosphere.

10. The loading station according to claim 1, wherein at least one of the ports (102a) is configured as a port for a sample transfer device (102) for transmission electron microscopy.

11. The loading station according to claim 1, wherein at least one of the ports (103a) is configured as a port for a sample transfer device (103) for light microscopy.

* * * * *